Figure 1:
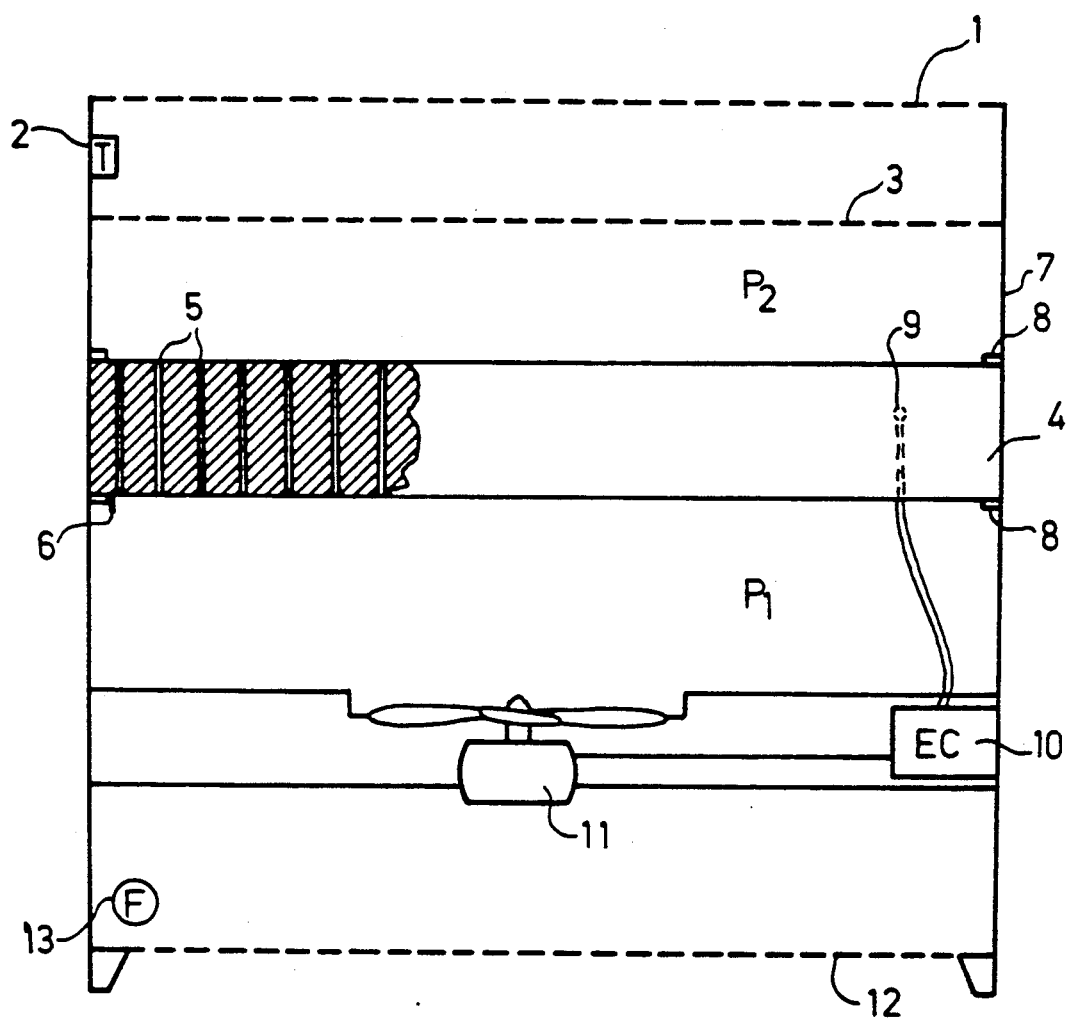

United States Patent [19]
Fiorenzano, Jr.

[11] Patent Number: 5,097,531
[45] Date of Patent: Mar. 17, 1992

[54] APPARATUS FOR THE OXIDATION OF PARTICLES SUSPENDED IN THE AIR

[75] Inventor: Alintor Fiorenzano, Jr., Rio de Janeiro, Brazil

[73] Assignee: Clover Electronica Limitada, Rio de Janeiro, Brazil

[21] Appl. No.: 201,125

[22] PCT Filed: Aug. 15, 1986

[86] PCT No.: PCT/BR86/00014
§ 371 Date: Apr. 4, 1988
§ 102(e) Date: Apr. 4, 1988

[87] PCT Pub. No.: WO88/01181
PCT Pub. Date: Feb. 25, 1988

[51] Int. Cl.$^5$ .............................. H05B 1/00
[52] U.S. Cl. ........................... 392/356; 392/360
[58] Field of Search ............ 219/360, 366, 369, 370, 219/374, 375; 392/339, 342, 347, 350, 354, 355, 356, 358, 360, 368, 373, 374, 385, 391, 407–416, 480

[56] References Cited

U.S. PATENT DOCUMENTS

| | | | |
|---|---|---|---|
| 1,701,096 | 2/1929 | Bowling et al. | 392/356 |
| 2,710,907 | 6/1955 | Westberg et al. | 392/360 |
| 2,896,061 | 7/1959 | McMillan | 392/350 |
| 3,575,582 | 4/1971 | Covault | 392/356 |
| 3,884,292 | 5/1975 | Pessolano et al. | 392/350 X |
| 4,053,732 | 10/1977 | Carter | 392/358 |
| 4,369,029 | 1/1983 | Förster et al. | 392/480 |
| 4,668,855 | 5/1987 | Wilson et al. | 392/385 |
| 4,680,448 | 7/1987 | Fester | 392/356 |

FOREIGN PATENT DOCUMENTS

575620 10/1931 Fed. Rep. of Germany.

Primary Examiner—William M. Shoop, Jr.
Assistant Examiner—A. Jonathan Wysocki
Attorney, Agent, or Firm—Beveridge, DeGrandi & Weilacher

[57] ABSTRACT

An apparatus for the oxidation of particles suspended in the air with a refractory material block (4) provided with small volume ducts (5) inside which s resistive wire is passed in order to generate a higher power density. The maximum volume of the ducts (5) is $10^3 m^3$ and its maximum cross section area is 1 cm$^2$, the ducts being dimensioned in such a way that the minimum permanence time of the air mass in their interior is 1 second and the minimum power density is equal 50 KW/m$^3$. The block (4) may be disposed inside a metal box (7) which also contains a fan, the motor (11) of which is commanded by an electronic control circuit (10) that receives signals related to the block temperature by a thermal sensor (9) disposed within the block.

10 Claims, 4 Drawing Sheets

APPARATUS FOR THE OXIDATION OF PARTICLES SUSPENDED IN THE AIR

The present invention refers to an apparatus for the oxidation of particles suspended in the air, comprising a plurality of ducts open at both ends, within which is disposed a resistive wire.

Brazilian patent application PI 8302255 of the same inventor discloses an air sterilization system using a high temperature gradient ducts, inside which resistive nickel-chromium wires are axially introduced, the ducts being preferably cylindrical.

Experiments have demonstrated that such a system is viable only if some parameters are observed which are not considered in said application.

The present invention aims to provide an improvement of said system, in order to permit a rapid oxidation of particle suspended in the air, under application of a relatively low total power and with high efficiency.

This aim is achieved by the invention due to the fact that said ducts 5 have a maximum volume of $10^{-3}$ m$^3$ and a maximum cross section area of 1 cm$^2$, the length and cross section being dimensioned in such a way that the minimum permanence time of the air mass within the ducts 5 is 0.01 second and the minimum power density within the ducts is 50 KW/m$^3$.

Experiments have shown that by maintaining the above parameters it is possible to achieve a sterilization with high efficiency and low costs in closed ambience.

The present invention provides a new way of achieving the oxidation of particles suspended in the air in ambience, should they be alive forms or inaminated, reducing also the relative humidity in a surprisingly efficient manner. The high oxidation rate, which is achieved inside the ducts, promotes the elimination of microorganisms from the air by means of the oxidation of the proteins as well as eliminates odors and oxidates some molecular forms of gases such as CO (toxicant) transforming it $CO_2$ (inert to human organism). It refers to an improvement of extreme importance on the asepsis methods, pollution control, conservation of works of art, conservation of agricultural products and the like.

According to a preferred embodiment, the present invention is basically composed by three systems: the first one is a refractory material block provided with more than a hundred capillaries whereby a high power density is generated; the second one is a control system and the third is a propulsive system.

Those systems are interconnected in such a way that the set works as an only system.

A preferred embodiment consists in executing the ducts as cylindrical perforations in a refractory block disposed inside a box, which is provided below the block, with a fan for controlling the air flow, the fan being actuated by means of an electronic circuit, which, by its turn, is connected to a temperature sensor disposed within the block. This embodiment will be described afterwards in more detail.

An embodiment example utilizes a refractory material block of 7 cm thickness in which 120 trespassing cylindrical ducts without 2.0 to 2.5 mm diameter are provided, whereby a NiCr filament with a resistivity of 24Ω/m is axially passed through the ducts, dissipating a total power of 500 W. The power dissipated in each duct is 3.5 W for a total length to the NiCr filament of 10 m.

The refractory material block has, preferably, the following weight composition: 45% SiO, 42% $Al_2O_3$, 4% $ZrO_2$, 1% $TiO_2$, 6% CaO and 2% MgO. This refractory material has a thermal conductivity coefficient K=0,300 Kcal/h°C. m/m$^2$at a temperature of 600° C.

Effecting the calculation for this embodiment example, it is found:

a) The power density within each duct (up):

$up$ = duct power/duct volume, where duct power = 3,5 W $$\text{duct volume} = \frac{\pi D^2}{4} \times L = \pi \times \frac{(2 \times 10^{-3})^2}{4} \times 7 \times 10^{-2}\ m^3 = 2{,}2 \times 10^{-7}\ m^3$$

up = 15,90 × 10$^6$ W/m$^3$,
what represents an extraordinarily high value.

b) Energy density transformed within each duct (uEtd): $uEtd = up \times t$, where t is the average permanence time of the air mass within the duct. For t=0, 1s: $uEtd = 1.59 \times 10^6 J/m^3$ Considering the importance of the radiation in the infrared band in the oxidation process of particle:

c) Energy density in the infrared band (uEir):

$$uEir = 1.59 \times 10^4\ J/m^3,$$

assuming that 1% of uEtd is in the infrared band.

d) Energy of each photon generated with the wave length $$\lambda_{max}\ (E_{max}):\ E_{max} = \frac{hc}{\lambda_{max}},$$

where $$h = 6{,}63 \times 10^{-34}\ Js$$

$$c = 3 \times 10^8\ m/s$$

$$\lambda_{max} = \frac{2{,}898 \times 10^{-3}}{T}\ m/°K.$$

then $$T = 500°\ C. = 773°\ K.$$

$$E_{max} = 6{,}63 \times 10^{-34} \times \frac{3 \times 10^8}{2{,}898 \times 10^{-3}/773}$$

$$E_{max} = 5{,}30 \times 10^{-20}\ J$$

e) Number of photons per cubic meter ($N\lambda_{max}$): $N\lambda_{max} = 3.00 \times 10^{23}$ photons/m$^3$, which is a rather high number.

Associating those results to the scientific knowledge, one verifies that the air mass carrying suspended particles has those particles oxidated in an undoubtful way when submitted to conditions of thermal power and infrared power together with the Nickel of the filament which acts as a catalyst.

The control of the air flow through the ducts, has the objective of making the permanence time of the air mass as well as the temperature within the ducts not affected by the environment conditions. This is done by means of a signal generated by a Constant Iron sensor, i.e., a thermocouple (other kinds of thermal sensors can be used) which generates a control signal by means of an electronic circuit whose outlet controls the air flow of a fan.

Figure 2:
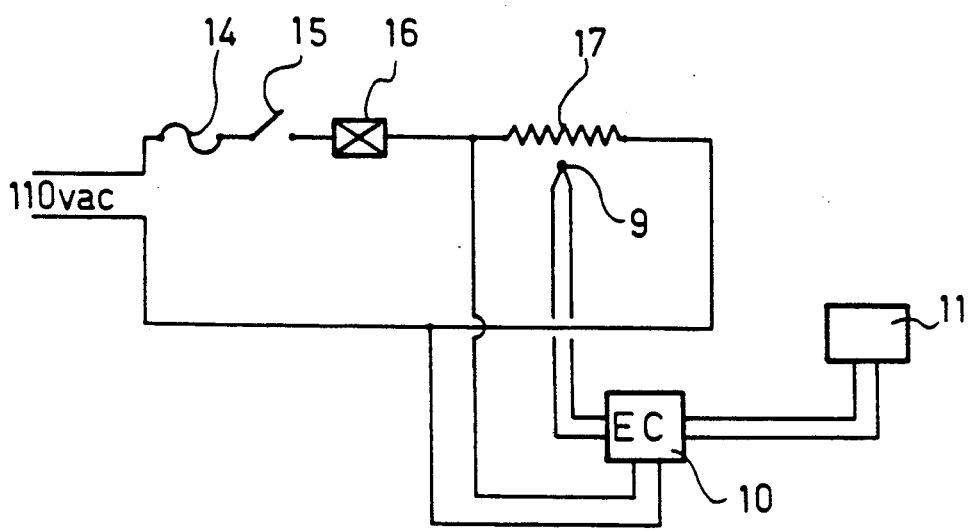
Figure 3:
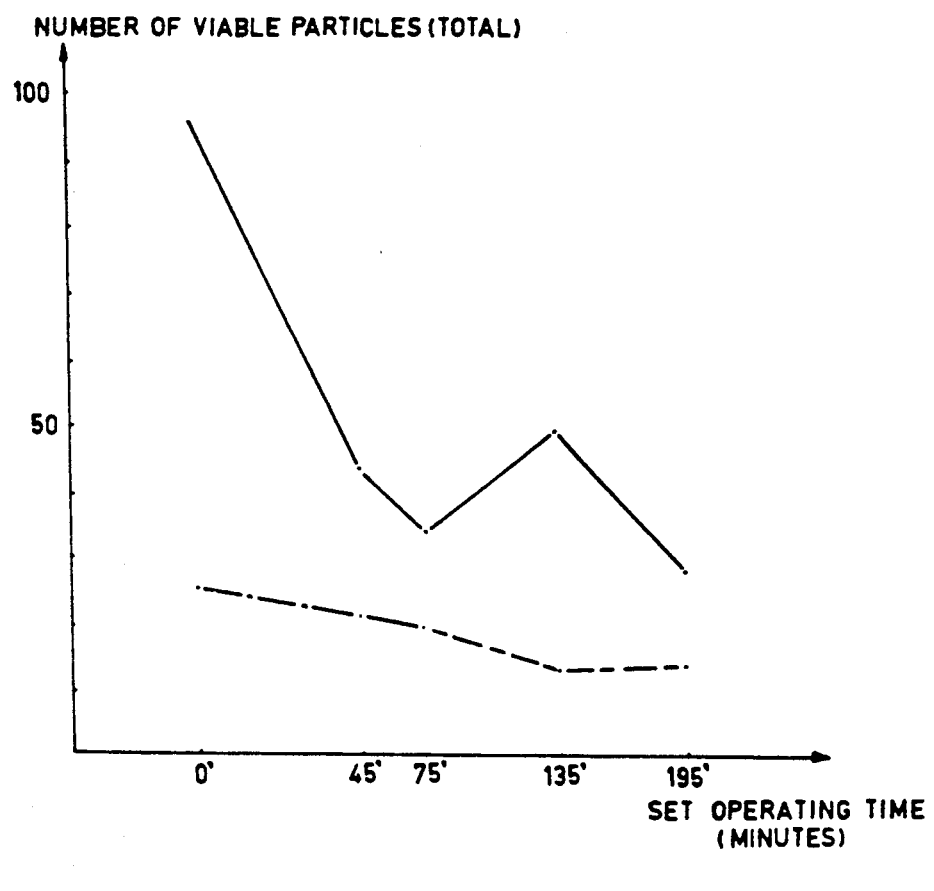
Figure 4:
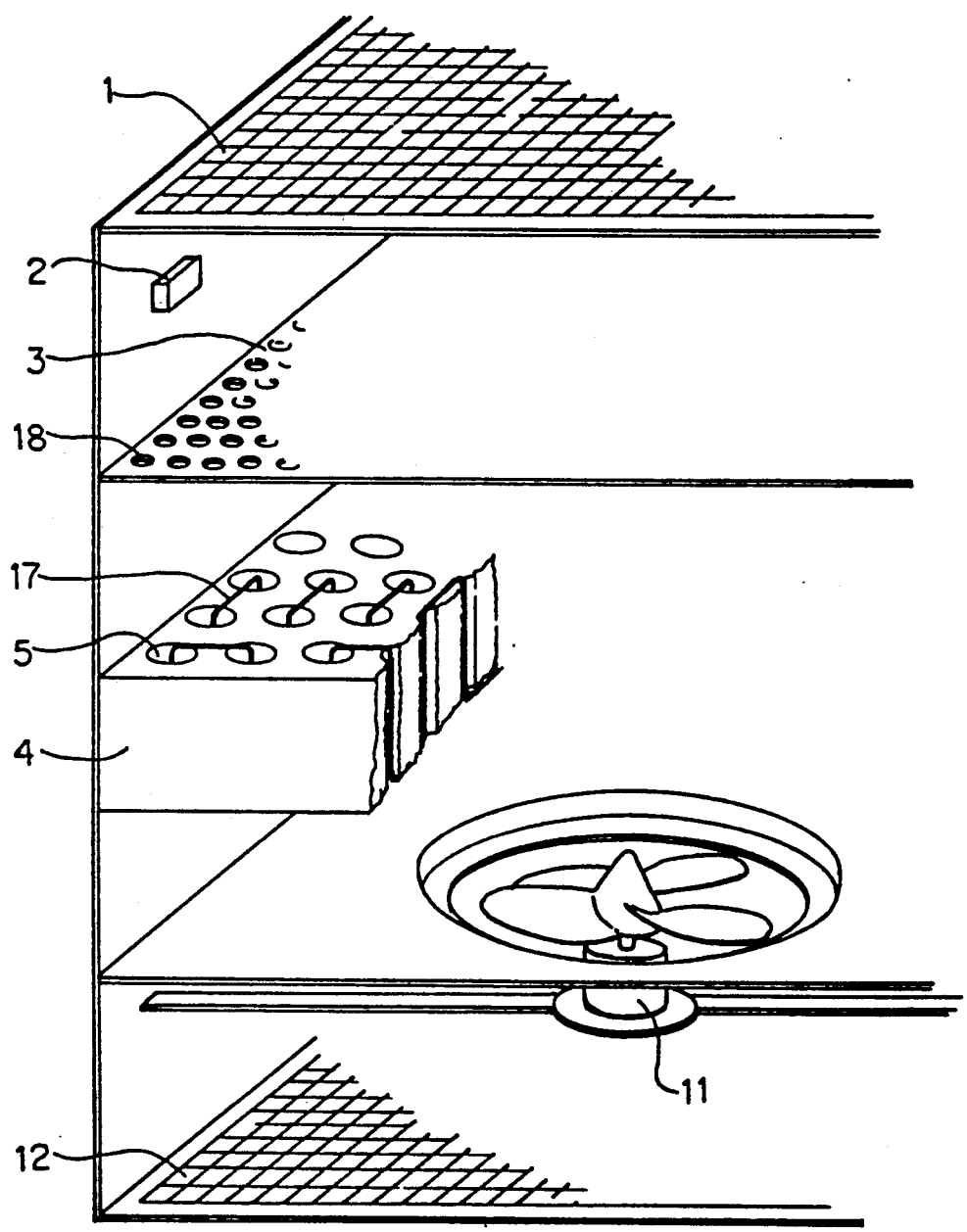

The apparatus will be described, based on an embodiment example represented on the drawings. The figures show schematically:

FIG. 1 a side sectioned view of the apparatus;

FIG. 2 the basic electric circuit of the apparatus of FIG. 1;

FIG. 3 a graphic of an experiment carried by the Brazilian Ministry of Health; and, FIG. 4 is a partial simplified perspective view of the embodiment of FIG. 1.

The apparatus represented in FIG. 1 is disposed within a metal box 7 provided with superior 1 and inferior 12 protecting network screen. The refractory block 4, within which are executed the small volume ducts 5, is fixed to the box 7 by fixing pieces 8. The piece 6 serves for the fixation of the electric wire, which is passed through the ducts 5 in a tensive way in the art of a "needle-work", the wire not being represented in FIG. 1 in order to simplify it.

The electronic control circuit 10 is connected to a thermal sensor 9 which is allocated within the block 4, although it is also possible to dispose the sensor on the outlet of the ducts. The control system of the fan motor 11 can be executed as a continuous control, but in this example it is executed as an ON-OFF type with hysteresis, as represented in FIG. 2.

A perforated inox steel 3, provided with perforations with a diameter of about 2 mm, is fixed within the box 7 above the block 4, in order to actuate as heat exchanger, cooling the air that leaves the box, a thermostat or thermal circuit breaker 2 being disposed above the perforated plate 3 to turn off the apparatus if the temperature of the air leaving the box 7 exceeds a predetermined limit.

A fuse 13 guarantees the apparatus against possible overload.

On the scheme represented on FIG. 2 there are provided a Slow-Blow type fuse 14 of 5 amperes which corresponds to fuse 13 of FIG. 1, an ON-OFF type switch 15, a thermostate 16 with disarm at 70° C. which corresponds to thermostat 2 of FIG. 1, a Ni-Cr filament 17 of 24.2Ω/m×500 W for the 110 V version, a thermal sensor 9 of the thermocouple type, as well as the fan's motor 11 and the electronic control circuit 10.

The electronic control circuit 10 operates in such a way, that when it receives a signal from the thermal sensor 9 indicating that the temperature on the block 4 reached a predetermined maximum value, it activates the fan's motor 11, increasing the pressure P1 below the block and, thus, increasing the air flow speed through the ducts, the pressure P2 above the block being smaller than P1. The raise of air flow causes the temperature to fall until it reaches a predetermined minimum value, when, then, the electronic control circuit 10 deactivates the fan. With this system it is possible to maintain the temperature and the permanence time of the air within the ducts within predetermined values.

FIG. 4 shows the resistive wire 17 passing through the cylindrical ducts 5 of the refractory block 4. As can be seen, a single wire 17 extends axially through the ducts 5. The perforated plate 3 is provided with several perforations 18. A breaker 2 corresponds to the thermostat 16 of FIG. 2, and this breaker is located above the plate 3.

A model based on the above described example supplied a mean flow of 35 m³/h of sterilized air for a room temperature of 30° C. and relative humidity of 85%.

The temperature variation, in its maximum and minimum spots through the ducts, was of 95° C. in the inferior portion, 450° C. at 6 cm above the inferior portion and 300° C. on the outlet of the ducts at 7 cm.

The model proved to be efficient in the reduction of biological activity in the air in a room of 250 cubic meters volume. Thus, it was verified that the present invention does not heat significantly the room, being destinated only to the air treatment, reducing the relative humidity and the biological activity.

For instance, it may be mentioned that the average thermal irradiation of a grown-up person is about 100 Watts. Therefore the 500 W model of the present invention is thermically equivalent to 5 people within a room of about 100 square meters and 2.5 meter high. This demonstrates that its load on the cooling systems is insignificant, thus being of great utility in rooms where there is no air renovation.

Since it does not produce a significant heating of the room, due to its low power per air volume unit relation, the present invention is not dependent upon on the climatization form and can be used indiscriminately.

In an experiment carried in Bremen University (German Federal Republic) with an apparatus of the present type inside a garbage room of 21.2 m³ (3.67 m×2.88 m×2.00m), the following results were found:

| parameters of experiment operation time of the apparatus: 64 h number of apparatus: 2 results table | | | |
|---|---|---|---|
| germs content | before | after | reduction |
| total germs content | 14 | 10 | 28% |
| yeast + mould | 5 | 1 | 80% |
| enterobacteriacese | 4 | — | 100% |
| bac. cereus | 15 | 3 | 80% |
| encubating time: 7 days | | | |

Conclusions : each apparatus could reduce, e.g., the yeast + mould incidence in 80% for a room of 10 m³. In the gross, it seems that the apparatus used in the experiment permit an advantageous germ elimination effect.

Yet, another experiment carried in the Brazilian Ministry of Health—Oswaldo Cruz Foundation—National Institute for Quality Control in Health resulted in a particle reduction as represented on FIG. 3. The parameters of the experiment were as follow:

specification of se: flow = 9 m³/h
volume of the test room: 25.80 m³
number of sterilizers: 3
experimental method: growing of colonies of microorganisms (fungi and bacteria) in Petri dishes, in blood agar and Sabourand's agar media exposed to the environment for 15 minutes.

The process is repeated with different set operating periods (0 min, 45 min, 75 min, 135 min and 195 min).

Conclusions and remarks were stated as follow:

The exponential pattern $e^{\bar{y}} = e^{93.106}x^{-11.83}$ is appropriate for representing the decrease of viable particles with set operating time.

Both factors, set operation time and also the day the experiments were carried out are significant. We should interpret the difference observed as a consequence rather of the (successive) day than of the fact that the experimenter remained in the room or circulated entering and leaving it.

Considering that the experiments were carried on on succeeding days, a large decrease evident in the number of viable particles obtained in experiment II, and such difference is statistically significant.

As can be seen from the graph, the number of particles remains much stabler, though decreasing with time, on the second day, so that there is a stabilization of the general level of particles in the environment. The difference between the experiments (days) proves highly significant in the beginning (0') and at 135'. In the latter case it is likely that a variation has occurred in the voltage, causing the number of particles to increase, contrary to expectation.

The significance of the interaction is reflected by the fact that the variations observed between set operation times depended on the day (1st or 2nd) the experiment was performed.

Accordingly, we may conclude that the general level of particles in the environment tends to vary in function of the initial concentration of particles. On the second day, the concentration is much smaller (a highly significant difference within $t_1 = 0'$ and the number of particles decreases with operation time, but not so sharply.

As a result of the general analysis applied, we conclude that the set is efficient in reducing the number of viable particles in the environment.

So the object in a second stage of the analysis, would then be to find out whether the reduction of the number of particles attains that minimum level of concentration which characterizes a sterile environment.

According to N.A.S.A. specifications, a sterile environment must contain no more than 0.0035 viable particles per liter.

Since the flow in the set is 9 cubic meters per hour and the volume of the room 25.80 cubic meters, we conclude that sterilization of the room would occur after approximately 2 hours 52 minutes or 172 minutes of set operation.

The present experiment used three (3) sets operating simultaneously, so room sterilization time would be reduced to 172 minutes divided by three, or 57 minutes, i.e. about one hour.

Considering the volume above the area where the Petri dishes were exposed to be approximately one cubic meter, we conclude that an index of 3.5 viable particles per cubic meter would represent a correct index of sterility to the environment.

In experiment I, the values were significant at the 5% level with 75' and 135', and almost significant (but that is no longer significant) at 195'; accordingly, one concludes that on that first day, when the room had an initial natural concentration of particles in the environment, *after 3 hours of operation* was the set able to reduce the environmental air to a level considered sterile.

In experiment II, i.e. on the second day, the differences were not significant, with much lower concentration, and in this case the atmosphere may be considered sterile.

I claim:

1. Apparatus for the oxidation of particles suspended in the air, comprising a refractory material block which is provided with a plurality of ducts open at both ends, a resistive wire being passed through the ducts, said ducts (5) having a maximum volume of $10^{-3}$ m$^3$ and a maximum cross section area of 1 cm$^2$, the length and cross section being dimensioned in such a way that the minimum permanence time of the air mass within the ducts is 0.01 second and the minimum power density within the ducts 50 KW/m$^3$.

2. Apparatus according to claim 1, characterized in that said ducts (5) have a maximum volume of $5 \times 10^{-5}$ m$^3$ and a maximum cross section area of 0.1 cm$^2$, the minimum permanence time of the air within the ducts (5) being equal to 0,1 second and the minimum power density within the ducts being equal to 250 KW/m$^3$.

3. Apparatus according to claim 1, characterized in that said ducts (5) have a cross section area of 3 to 5 mm$^2$ and a length of about 7 cm.

4. Apparatus according to claim 1 or 3, characterized in that said ducts (5) are cylindrical having a round cross section with a diameter of 2.0 to 2.5 mm.

5. Apparatus according to claim 1, characterized in that a single NiCr wire is passed through all ducts, said wire having a relative resistivity of about 24.2Ω/m.

6. Apparatus according to claim 5, characterized in that the refractory material of said block (4) has a weight composition of 45% SiO$_2$, 42% Al$_2$O$_3$, 4% ZrO$_2$, 1% TiO$_2$, 6% CaO and 2% MgO.

7. Apparatus according to claim 5 or 6, characterized in that said refractory material block (4) is disposed within a box (7) which is provided with a fan, the motor (11) of the fan being controllable by an electronic control circuit (10) which is connected to a thermal sensor (9) disposed within the refractory material block (4).

8. Apparatus according to claim 7, characterized in that the electronic control circuit (10) comprises an ON-OFF type control to activate and deactivate the motor (11) of the fan, the electronic control circuit (10) being able to activate the motor (11) of the fan when the temperature on the refractory material block (4) reaches a predetermined maximum value and to desactivate it when said temperature decreases to a predetermined minimum value.

9. Apparatus according to claim 7, characterized in that the electronic control circuit (10) comprises a continuous type control to activate the motor (11) of the fan in various speeds depending on the temperature of the refractory material block (4).

10. Apparatus according to claim 7, characterized in that said box (7) comprises a perforated plate (3) disposed above the refractory material block (4), said perforated plate (3) being provided with a plurality of perforations with a diameter of about 2 mm.

* * * * *